United States Patent
Shimizu (10) Patent No.: US 10,266,473 B2
(45) Date of Patent: Apr. 23, 2019

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 15/540,177

(22) PCT Filed: May 25, 2017

(86) PCT No.: PCT/JP2017/019572
§ 371 (c)(1),
(2) Date: Jun. 27, 2017

(87) PCT Pub. No.: WO2018/078924
PCT Pub. Date: May 3, 2018

(65) Prior Publication Data
US 2018/0118649 A1    May 3, 2018

(30) Foreign Application Priority Data

Oct. 28, 2016  (JP) ................................ 2016-211922
Mar. 2, 2017   (JP) ................................ 2017-039388

(51) Int. Cl.
| | | |
|---|---|---|
| C07C 51/12 | (2006.01) | |
| C07C 51/44 | (2006.01) | |
| B01D 1/30 | (2006.01) | |
| B01D 53/14 | (2006.01) | |
| B01D 3/14 | (2006.01) | |

(52) U.S. Cl.
CPC ............... *C07C 51/12* (2013.01); *B01D 1/30* (2013.01); *B01D 3/148* (2013.01); *B01D 53/1418* (2013.01); *C07C 51/44* (2013.01)

(58) Field of Classification Search
None
See application file for complete search history.

(56) References Cited

U.S. PATENT DOCUMENTS

| | | | |
|---|---|---|---|
| 5,237,097 A | 8/1993 | Smith et al. | |
| 2008/0081933 A1 | 4/2008 | Bastings et al. | |
| 2011/0009665 A1 | 1/2011 | Scates | |
| 2013/0140722 A1* | 6/2013 | Zinobile | B01D 3/32 261/114.1 |
| 2015/0368176 A1 | 12/2015 | Miura et al. | |
| 2017/0190649 A1 | 7/2017 | Hennigan | |

FOREIGN PATENT DOCUMENTS

| | | |
|---|---|---|
| CN | 200984467 Y | 12/2007 |
| CN | 201415064 Y | 3/2010 |
| EP | 0 441 260 A1 | 8/1991 |
| EP | 2653459 A1 | 10/2013 |
| EP | 2949640 A1 | 12/2015 |
| JP | 5-194300 A | 8/1993 |
| JP | 2009-539932 A | 11/2009 |
| JP | 2012-532867 A | 12/2012 |
| WO | WO 2007/144360 A2 | 12/2007 |
| WO | WO 2011/005304 A2 | 1/2011 |
| WO | WO 2014/115826 A1 | 7/2014 |
| WO | WO 2016/020410 A1 | 2/2016 |

OTHER PUBLICATIONS

Japanese Notification of Reasons for Refusal for Application No. 2017-533361, dated Jul. 10, 2018, with English language translation.
Translation of the Written Opinion of the International Searching Authority (Forms PCT/IB/310 and PCT/ISA/237) for International Application No. PCT/JP2017/019572, dated Nov. 17, 2017.
Extended European Search Report, dated Mar. 12, 2018, for European Application No. 17732014.0.
International Search Report and Written Opinion of the International Searching Authority (Forms PCT/ISA/237 and PCT/ISA/210) for International Application No. PCT/JP2017/019572, dated Aug. 29, 2017.

* cited by examiner

*Primary Examiner* — Ana Z Muresan
(74) *Attorney, Agent, or Firm* — Birch, Stewart, Kolasch & Birch, LLP (57) ABSTRACT

Provided is a method for producing acetic acid, which suppresses catalyst precipitation and accumulation in an evaporator, can efficiently recycle catalysts to a reaction vessel, and can contribute to maintenance and improvement in acetic acid productivity and securing of safety operation. In the method, the evaporator has a catalyst precipitation and accumulation prevention structure: (a) structure where inclination angle θ of inside wall surface of an inverted truncated conical cylindrical connection portion is 5° to 85°; and/or (b) structure where a vortex breaker comprising a plate-like vortex breaker main body and a leg is disposed such that the vortex breaker main body covers right above the connection portion of an evaporator bottom part to a residual liquid stream recycle line, and linear velocity r of the residual liquid stream passing through a gap between the vortex breaker main body and the evaporator bottom part is larger than 10 m/h.

9 Claims, 2 Drawing Sheets

METHOD FOR PRODUCING ACETIC ACID

TECHNICAL FIELD

The present invention relates to a method for producing acetic acid. The present application claims the priorities of Japanese Patent Application No. 2016-211922 filed in Japan on Oct. 28, 2016 and Japanese Patent Application No. 2017-039388 filed in Japan on Mar. 2, 2017, the contents of which are incorporated herein by reference in their entirety.

BACKGROUND ART

A carbonylation process of a methanol method is known as an industrial method for producing acetic acid. In this process, for example, methanol and carbon monoxide are reacted in the presence of a catalyst in a reaction vessel to produce acetic acid. The obtained reaction mixture is separated in an evaporator into a vapor phase containing acetic acid and lower boiling point components and a residual liquid phase containing acetic acid and the catalyst. The residual liquid phase is recycled to the reaction vessel while the vapor phase is separated by distillation into lower boiling point components and crude acetic acid. The crude acetic acid is further purified to obtain product acetic acid.

This carbonylation process of the methanol method has the major advantage that acetic acid can be efficiently produced from inexpensive raw materials, but presents the problem that the catalyst is easily precipitated. In this process, the prevention of the catalyst precipitation is an important challenge from the viewpoint of securing productivity by the maintenance of a catalyst concentration in the reaction vessel, and securing safety operation by the prevention of catalyst concentration variation in the reaction vessel. Among others, the most important challenges are to prevent catalyst precipitation in an evaporator where the catalyst is most easily precipitated, and to improve the rate of catalyst recycle from the bottom of the evaporator to the reaction vessel.

It has heretofore been known that a catalyst stabilizer such as lithium iodide is contained in a reaction solution in order to prevent catalyst precipitation. Also, a technique of improving the stability of carbon monoxide and a complex of an iodide ion and a metal is known which involves introducing a carbon monoxide-containing gas to the bottom of an evaporator to increase a CO partial pressure or the amount of CO dissolved in an evaporator bottom fraction. For example, Patent Literature 1 discloses a method for preventing catalyst precipitation in an evaporation step by introducing a carbon monoxide-containing gas stream to a separation zone in the step of transferring a carbonylation product solution to the separation zone maintained at a pressure lower than that of a reaction zone, subjecting a portion of the carbonylation product to flash separation, and circulating an unflashed carbonylation product solution to the reaction zone.

CITATION LIST

Patent Literature

Patent Literature 1: Japanese Patent Laid-Open No. 5-194300

SUMMARY OF INVENTION

Technical Problem

However, in the method described above, catalyst precipitation in an evaporator cannot always be sufficiently suppressed, and a phenomenon is seen in which a catalyst precipitated in the evaporator is accumulated. Thus, an object of the present invention is to provide a method for producing acetic acid, which suppresses catalyst precipitation and accumulation in an evaporator, can efficiently recycle catalysts to a reaction vessel, and can contribute to maintenance and improvement in acetic acid productivity and securing of safety operation.

Solution to Problem

The present inventors have conducted diligent studies to attain the object and consequently completed the present invention by finding that an evaporator is provided with a specific catalyst precipitation and accumulation prevention structure, whereby catalysts can be efficiently recycled to a reaction vessel, and decrease in catalyst concentration in the reaction vessel can be suppressed, and hence, this can contribute to maintenance and improvement in acetic acid productivity and securing of safety operation.

Specifically, the present invention provides a method for producing acetic acid, comprising:

a carbonylation reaction step of reacting methanol with carbon monoxide in the presence of a catalyst system comprising a metal catalyst and methyl iodide, acetic acid, methyl acetate, and water in a reaction vessel to produce acetic acid;

an evaporation step of separating the reaction mixture obtained in the carbonylation reaction step into a vapor stream and a residual liquid stream in an evaporator;

a residual liquid stream recycle step of bringing the residual liquid stream back to the reaction vessel; and a distillation step of distilling the vapor stream to purify acetic acid, wherein the evaporator has a body part connected with a reaction mixture feed line, a top part connected with a vapor stream discharge line, and a bottom part connected with a residual liquid stream recycle line, the body part having an upper cylindrical portion having a large diameter, a lower cylindrical portion having a small diameter, and an inverted truncated conical cylindrical connection portion which joins the upper cylindrical portion and the lower cylindrical portion, and has at least one of the following catalyst precipitation and accumulation prevention structures (a) and (b):

(a) a structure where an inclination angle θ of inside wall surface of the inverted truncated conical cylindrical connection portion of the evaporator is 5° to 85°; and (b) a structure where a vortex breaker comprising a plate-like vortex breaker main body and a leg which horizontally supports the vortex breaker main body is disposed such that the vortex breaker main body covers right above the connection portion of the evaporator bottom part to the residual liquid stream recycle line, and the structure is designed such that a linear velocity r of the residual liquid stream passing through a gap between the circumferential end of the vortex breaker main body and the inside bottom surface of the evaporator bottom part is larger than 10 m/h.

The catalyst system may further comprise an ionic iodide.

In the structure (a), it is preferred that the inclination angle θ of inside wall surface of the inverted truncated conical cylindrical connection portion of the evaporator should be 10° to 80°. The inclination angle θ is further preferably 20° to 75°, particularly preferably 30° to 75°.

In the structure (b), it is preferred that the bottom part of the evaporator and/or the residual liquid stream recycle line should be further connected with a carbon monoxide-containing gas introduction line. In this case, it is preferred that a carbon monoxide-containing gas should be introduced at not less than 0.02 NL/kg with respect to the amount of the residual liquid stream discharged, from the carbon monoxide-containing gas introduction line.

It is preferred that the distillation step should comprise a lower boiling point component removal step of separating the vapor stream by distillation into an overhead stream rich in at least one lower boiling point component selected from methyl iodide and acetaldehyde and an acetic acid stream rich in acetic acid. In this case, the method may have an acetaldehyde separation and removal step for separating at least acetaldehyde from the overhead stream.

It is preferred that the production method of the present invention should further comprise a scrubber step (scrubbing step) of separating offgas from the process into a stream rich in carbon monoxide and a stream rich in acetic acid by absorption treatment with an absorption solvent containing at least acetic acid and/or methanol.

Advantageous Effects of Invention

According to the present invention, an evaporator has a structure where an inclination angle of inside wall surface of an inverted truncated conical cylindrical connection portion which joins an upper cylindrical portion having a large diameter and a lower cylindrical portion having a small diameter in an evaporator body part is in a specific range, and/or a structure designed such that a linear velocity of a residual liquid stream passing through a gap between a vortex breaker disposed in the evaporator and the bottom surface of the evaporator is not less than a specific value. Therefore, catalyst precipitation and accumulation in the evaporator can be significantly suppressed, and catalysts can be efficiently recycled to the reaction vessel. Therefore, a catalyst concentration in the reaction vessel is kept constant. This can make a significant contribution to maintenance and improvement in acetic acid productivity and securing of safety operation.

DESCRIPTION OF EMBODIMENTS

Figure 1:
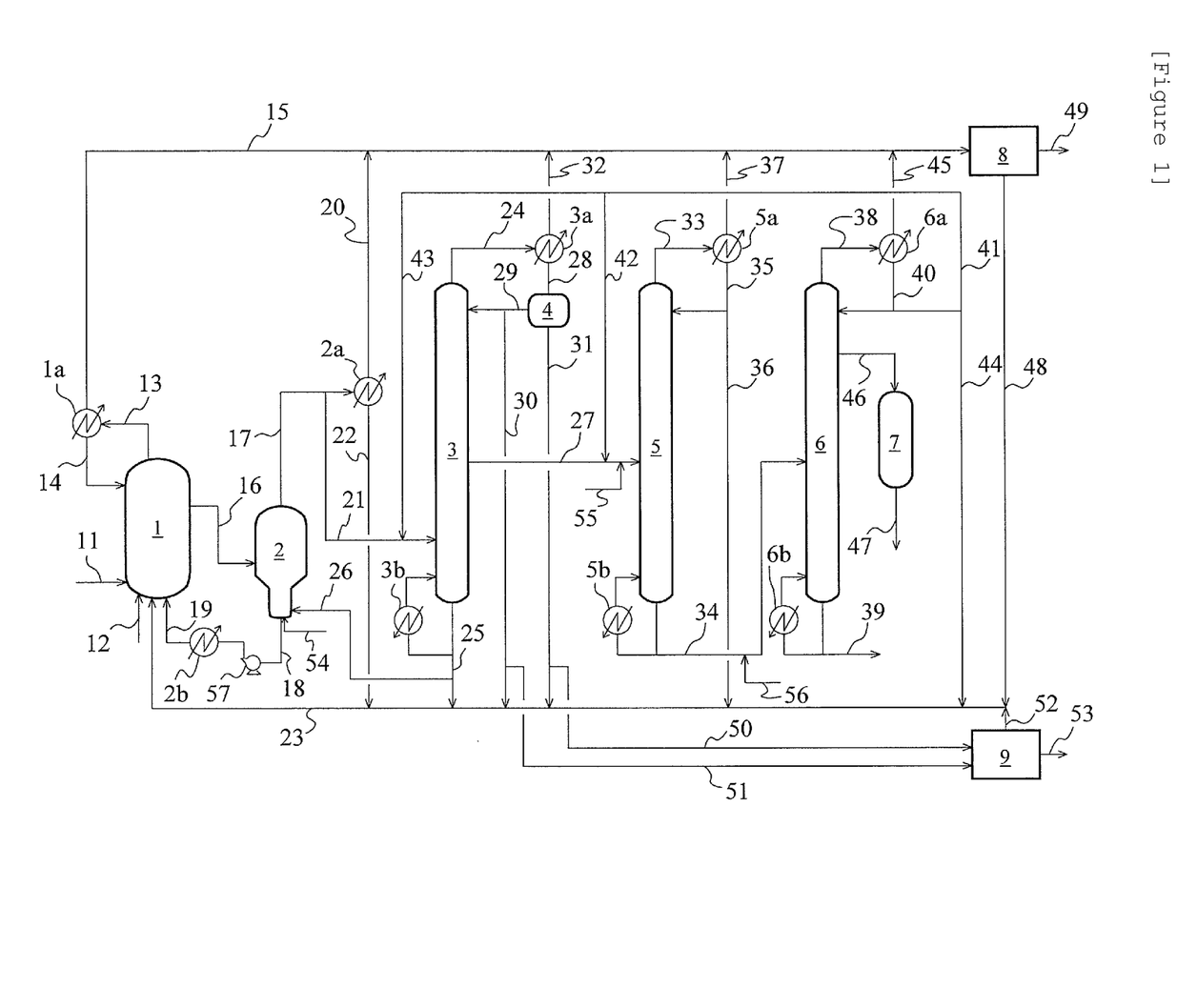
FIG. 1 is an acetic acid production flow diagram showing one embodiment of the present invention.

FIG. 1 is an acetic acid production flow diagram showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. The first distillation step, the second distillation step, and the third distillation step are included in the "distillation step to purify acetic acid" according to the present invention. In the present invention, the steps are not limited to those described above and may exclude, particularly, equipment of the distillation column 6, the ion exchange resin column 7, the acetaldehyde separation and removal system 9 (acetaldehyde removal column, etc.).

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \tag{1}$$

The raw materials in the reaction mixture are methanol in a liquid state and carbon monoxide in a gaseous state. Methanol is continuously fed at a predetermined flow rate to the reaction vessel 1 from a methanol reservoir (not shown) via the line 11. Carbon monoxide is continuously fed at a predetermined flow rate to the reaction vessel 1 from a carbon monoxide reservoir (not shown) via the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (in terms of the metal) of the catalyst in the reaction mixture is, for example, 200 to 5000 ppm by mass, preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. In addition, when an iridium catalyst or the like is used, for example, a ruthenium compound or an osmium compound can be used as a co-catalyst. The amount of these compounds to be used as the total amount is, for example 0.1 to 30 moles (in terms of metal), preferably 0.5 to 15 moles (in terms of metal) based on 1 mole of iridium (in terms of metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, formic acid, propionic acid, and alkyl iodides such as hexyl iodide and decyl iodide.

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.5 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 via the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a via the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a via the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 via the recycle line 48 and recycled. A gas after the capturing of the useful components is discarded via the line 49. The gas discharged from the line 49 can be used as a CO source to be introduced to the bottom part 205 of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 via the line 16.

The evaporator 2 is a unit for performing the evaporation step (flash step). This evaporation step is a step for separating the reaction mixture continuously introduced to the evaporator 2 via the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, and propionic acid and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 via the line 21. The acetic acid concentration of the vapor stream is, for example, 50 to 85% by mass, preferably 55 to 75% by mass. The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 via the line 18 using the pump 57. The heat exchanger 2b cools the residual liquid stream from the evaporator 2. The cooled residual liquid stream is continuously introduced to the reaction vessel 1 from the heat exchanger 2b via the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

Figure 2:
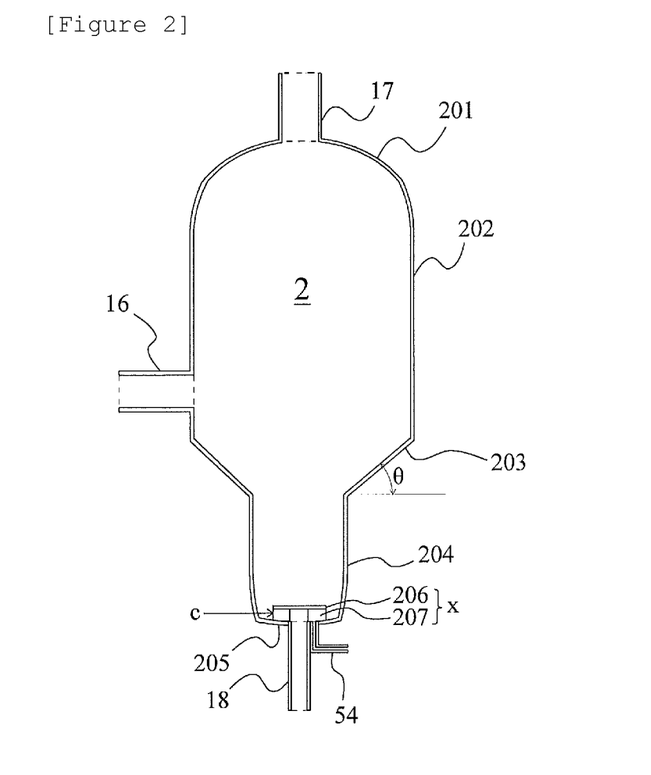
FIG. 2 is a schematic cross-sectional view of an evaporator showing one embodiment of the present invention.

FIG. 2 is a schematic cross-sectional view of an evaporator showing one embodiment of the present invention. The evaporator 2 has a body part connected with the reaction mixture feed line 16, a top part 201 connected with the vapor stream discharge line 17, and a bottom part 205 connected with the residual liquid stream recycle line 18. The body part has an upper cylindrical portion 202 having a large diameter, a lower cylindrical portion 204 having a small diameter, and an inverted truncated conical cylindrical connection portion 203 which joins the upper cylindrical portion 202 and the lower cylindrical portion 204. The reaction mixture from the reaction vessel 1 is introduced into the evaporator 2 from the reaction mixture feed line 16, and a portion of the reaction mixture is evaporated into a vapor, which is then discharged from the vapor stream discharge line 17. A component that has not been evaporated in the reaction mixture is retained in the lower cylindrical portion 204 and brought as an evaporator bottom fraction (residual liquid stream) back to the reaction vessel 1 through the residual liquid stream recycle line 18 connected to the bottom part 205, and the line 19. The upper cylindrical portion 202 functions as space to be fed with a vapor, and the lower cylindrical portion 204 functions as a reservoir for a residual liquid that has not been volatilized. Therefore, the upper cylindrical portion 202 is designed to have a large diameter, and the lower cylindrical portion 204 is designed to have a small diameter.

It is preferred that the bottom part 205 of the evaporator 2 and/or the residual liquid stream recycle line (line 18 and/or line 19) should be connected with a carbon monoxide-containing gas introduction line 54 for introducing a carbon monoxide-containing gas. Carbon monoxide is introduced to a residual liquid retained in the lower cylindrical portion 204 of the evaporator 2 or to a residual liquid stream passing through the residual liquid stream recycle lines 18 and 19 (particularly, the line 18) to thereby increase the amount of carbon monoxide dissolved in the residual liquid stream. Thus, the stability of the catalyst is enhanced, and the precipitation and accumulation of the catalyst can be prevented. The content of the carbon monoxide in the carbon monoxide-containing gas to be introduced is, for example, not less than 10% by mass, preferably not less than 20% by mass, further preferably not less than 40% by mass, particularly preferably not less than 60% by mass.

Figure 3:
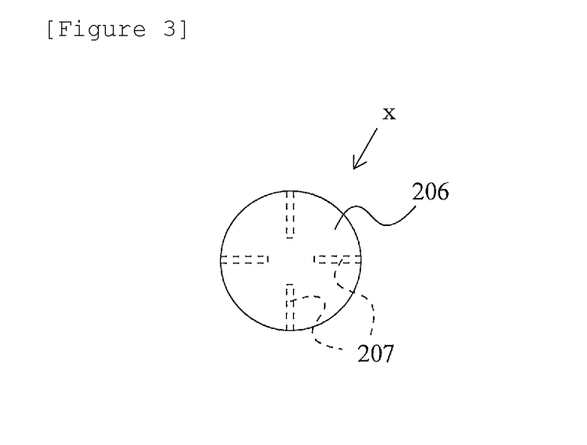
FIG. 3 is a plane view of a vortex breaker that is placed in the evaporator showing one embodiment of the present invention.

In the evaporator 2, it is preferred that a vortex breaker x should be disposed near the bottom part 205 of the evaporator 2 in order to prevent a temporarily volatilized vapor from flowing into the residual liquid stream recycle line 18 due to entrainment by a liquid that has not been volatilized. If a large amount of a gas flows into the bottom part 205, the pump 57 (catalyst circulation pump) for sending the residual liquid stream to the reaction vessel 1 might cause cavitation, resulting in breakage of the pump. FIG. 3 is a plane view (viewed from above) of a vortex breaker that is placed in the evaporator showing one embodiment of the present invention. The vortex breaker x consists of a plate-like vortex breaker main body 206 and legs 207 for horizontally supporting the vortex breaker main body 206. A plurality of legs 207 are preferred for stabilization. The legs 207 can be fixed to the inside bottom surface of the bottom part 205 of the evaporator 2. It is preferred that the plate-like vortex breaker main body 206 should be disposed so as to cover right above the connection portion of the bottom part 205 of the evaporator 2 to the residual liquid stream recycle line 18. The plate-like vortex breaker main body 206 may have a flat plate shape or may have a plate shape having lower or upper convex-curved surface.

In the present invention, the evaporator 2 has at least one of the following catalyst precipitation and accumulation prevention structures (a) and (b):

(a) a structure where an inclination angle (angle with respect to the horizontal plane) θ of inside wall surface of the inverted truncated conical cylindrical connection portion 203 of the evaporator 2 is 5° to 85°; and (b) a structure where the vortex breaker x consisting of the plate-like vortex breaker main body 206 and the legs 207 which horizontally support the vortex breaker main body 206 is disposed such that the vortex breaker main body 206 covers right above the connection portion of the evaporator bottom part 205 to the residual liquid stream recycle line 18, and the structure is designed such that a linear velocity r of the residual liquid stream passing through a gap c between the circumferential end of the vortex breaker main body 206 and the inside bottom surface of the evaporator bottom part 205 is larger than 10 m/h.

In the case where the evaporator 2 has the structure (a), even if a catalyst precipitated in the evaporator 2 is accumulated on the inside wall surface of the inverted truncated conical cylindrical connection portion 203, such a catalyst is entrained by a falling non-volatilized liquid in the reaction mixture introduced from the line 16 and arrives at the bottom part 205 of the evaporator 2, because the inclination angle of inside wall surface of the connection portion 203 is not less than the given value. Then, the catalyst is recycled to the reaction vessel 1 via the residual liquid stream recycle lines 18 and 19. Fine particles of the precipitated catalyst recycled to the reaction vessel 1 without remaining in the evaporator 2 are redissolved in the reaction vessel 1 having a high carbon monoxide partial pressure. As a result, decrease in catalyst concentration in the reaction vessel is suppressed. Thus, reduction or variation in the amount of acetic acid produced can be prevented. The inclination angle θ of inside wall surface of the inverted truncated conical cylindrical connection portion 203 can be in the range of 5° to 85°. The lower limit of the inclination angle θ is preferably 10°, more preferably 20°, further preferably 30°, particularly preferably 35° (in particular, 40°), and the upper limit of the inclination angle θ is preferably 80°, more preferably 75°, further preferably 70°. If the inclination angle θ is less than 5°, the precipitated catalyst is easily deposited on the inside wall surface of the connection portion 203. Thus, the amount of the catalyst recycled to the reaction vessel 1 is decreased to decrease the catalyst concentration in the reaction vessel 1, resulting in reduction in the amount of acetic acid produced. An inclination angle θ of more than 85° is not preferred because the length in the height direction of the inverted truncated conical cylindrical connection portion 203 is increased so that the total size of the evaporator 2 is increased.

In the case where the evaporator 2 has the structure (b), even if a catalyst is precipitated in the vicinity of the bottom part 205 of the evaporator 2, the precipitated catalyst is vigorously entrained by the residual liquid stream and flows into the residual liquid stream recycle line 18, because the linear velocity r of the residual liquid stream passing through the gap c between the circumferential end of the vortex breaker main body 206 and the inside bottom surface of the evaporator bottom part 205 is large. Then, the catalyst is recycled to the reaction vessel 1 via the line 19. The precipitated catalyst thus recycled is redissolved in the reaction vessel 1 as described above. Therefore, the catalyst concentration in the reaction vessel 1 can be kept at the desired value. Thus, reduction or variation in the amount of acetic acid produced can be prevented. Particularly, in the case where a carbon monoxide-containing gas is introduced to the bottom part of the evaporator 2 or the residual liquid stream recycle lines 18 and 19, the carbon monoxide gas is prevented from ascending in the evaporator 2, at a fast linear velocity r of the residual liquid stream, and easily flows into the residual liquid stream recycle lines 18 and 19 from the bottom part 205 of the evaporator 2. Therefore, carbon monoxide concentrations (amounts of carbon monoxide dissolved) in the bottom part 205 of the evaporator 2 and the residual liquid stream recycle lines 18 and 19 where catalyst precipitation occurs significantly are elevated to thereby improve the stability of the catalyst. Therefore, reduction or variation in the amount of acetic acid produced in the reaction vessel 1 can be more reliably prevented. The linear velocity r can be a value of larger than 10 m/h and is preferably not less than 20 m/h, more preferably not less than 30 m/h, further preferably not less than 50 m/h, particularly preferably not less than 80 m/h (in particular, not less than 100 m/h). The upper limit of the r is, for example, 6000 m/h (particularly, 4000 m/h).

In the case where the linear velocity r is not more than 10 m/h, the proportion of a precipitated catalyst flowing into the residual liquid stream recycle line 18 due to entrainment by the residual liquid stream is decreased. Therefore, the amount of the catalyst recycled to the reaction vessel 1 is also decreased so that the amount of acetic acid produced is decreased. Also, even in the case where a carbon monoxide-containing gas is introduced to the bottom part 205 of the evaporator 2 or the residual liquid stream recycle lines 18 and 19, the introduced carbon monoxide-containing gas easily ascends in the evaporator 2 when the linear velocity r is not more than 10 m/h. Thus, the carbon monoxide-containing gas moves, together with flash gas of the evaporator 2, to the next step (distillation column (lower boiling point component removal column) 3 or condenser (heat removal condenser) 2a). Therefore, the effect (catalyst stabilizing effect) of carbon monoxide introduction is reduced. In the case where the linear velocity r is too large, pressure loss is increased so that a generated residual liquid stream may not be recycled. Alternatively, there arises the need of increasing a liquid depth in the evaporator 2. The linear velocity r (m/h) is determined by dividing the amount of the residual liquid stream discharged (flow rate of a liquid flowing through the residual liquid stream recycle line 18) ($m^3$/h) by a product of the length (distance) (m) of the gap c between the circumferential end of the vortex breaker main body 206 and the inside bottom surface of the evaporator bottom part 205, and the circumferential length (m) of the vortex breaker main body 206. The linear velocity r can be adjusted by changing the length (distance) of the gap c or the circumferential length of the vortex breaker main body 206.

In the case of introducing a carbon monoxide-containing gas to the bottom part 205 of the evaporator 2 or the residual liquid stream recycle lines 18 and 19, the total amount of the carbon monoxide-containing gas introduced is, for example, not less than 0.02 NL (normal litter)/kg, preferably not less than 0.05 NL/kg, further preferably not less than 0.1 NL/kg, with respect to the amount of the residual liquid stream discharged (flow rate of a liquid flowing through the residual liquid stream recycle line 18). The upper limit of the amount of the carbon monoxide-containing gas introduced is, for example, 5 NL/kg (preferably 3 NL/kg, more preferably 1 NL/kg). If the amount of the carbon monoxide-containing gas introduced is too small, the amount of CO dissolved is decreased so that the catalyst easily becomes unstable. In the case where the amount of the carbon monoxide-containing gas introduced is too large, the pump 57 might cause cavitation and be broken.

In the production method of the present invention, at a fast linear velocity r' of the residual liquid stream passing through the residual liquid stream recycle lines 18 and 19, even if a catalyst is precipitated, the precipitated catalyst is transported to the reaction vessel 1 while entrained by the residual liquid stream having the fast linear velocity. Therefore, the precipitated catalyst can be prevented from being accumulated in the residual liquid stream recycle lines 18 and 19. It is preferred that the linear velocity r' should be larger than 10 m/h in not less than 80% (preferably not less than 90%, further preferably not less than 95%) of the whole channel from the bottom (point of origin of the residual liquid stream recycle line 18) of the evaporator bottom part 205 to the reaction vessel 1. The linear velocity r' is more preferably not less than 100 m/h, further preferably not less than 500 m/h, particularly preferably not less than 1000 m/h, most preferably not less than 2000 m/h. The linear velocity r' (m/h) is determined by dividing the amount of the residual liquid stream recycled (flow rate of a liquid flowing through the residual liquid stream recycle line) ($m^3$/h) by the cross-sectional area ($m^2$) of the residual liquid stream recycle line.

Even in the case where the evaporator 2 has only one of the structure (a) and the structure (b), catalyst precipitation and accumulation in the evaporator 2 can be suppressed to a considerable extent. However, catalyst precipitation and accumulation in the evaporator 2 having both of the structure (a) and the structure (b) can be significantly decreased. Thus, acetic acid productivity in the reaction vessel 1 and operational safety can be drastically improved.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a via the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a via the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C.

The vapor stream from the evaporator 2 is continuously introduced to the distillation column 3 via the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a via the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a via the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 via the line 29, and another portion of the aqueous phase is introduced to the reaction vessel 1 via the lines 29, 30, and 23 and recycled. A portion of the organic phase is introduced to the reaction vessel 1 via the lines 31 and 23 and recycled. Another portion of the organic phase and/or a remaining portion of the aqueous phase is introduced to the acetaldehyde separation and removal system 9 via the lines 31 and 50 and/or the lines 30 and 51.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus via the line 53. The useful components (e.g., methyl iodide) contained in the organic phase and/or the aqueous phase are recycled to the reaction vessel 1 via the lines 52 and 23 and reused.

The gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a via the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 via the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 via the lines 25 and 26 and recycled, and another portion of the bottom fraction is continuously introduced to the reaction vessel 1 via the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream contains, in addition to acetic acid, for example, methyl iodide, hydrogen iodide, water, methyl acetate, dimethyl ether, methanol, acetaldehyde, formic acid, and propionic acid. The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 via the line 27.

To the first acetic acid stream flowing through the line 27, potassium hydroxide can be fed or added via the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. The distillation column 5 consists of, for example, a distillation column such as a plate column or a packed column. In the case of adopting a plate column as the distillation column 5, the theoretical number of plates thereof is, for example, 5 to 50, and the reflux ratio is, for example, 0.2 to 3000 according to the theoretical number of plates. In the inside of the distillation column 5 in the second distillation step, the column top pressure is set to, for example, 150 to 250 kPa (gauge pressure), and the column bottom pressure is higher than the column top pressure and is set to, for example, 160 to 290 kPa (gauge pressure). In the inside of the distillation column 5 in the second distillation step, the column top temperature is, for example, a temperature of higher than the boiling point of water and lower than the boiling point of acetic acid at the set column top pressure and is set to 130 to 160° C., and the column bottom temperature is, for example, a temperature of not less than the boiling point of acetic acid at the set column bottom pressure and is set to 150 to 175° C.

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a via the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a via the line 35. Another portion of the condensate portion is continuously introduced to the reaction vessel 1 from the condenser 5a via the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a via the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 via the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5 and contains, for example, propionic acid, potassium acetate (in the case of feeding potassium hydroxide to the line 27, etc.), and the entrained catalyst and co-catalyst mentioned above. This bottom fraction contains acetic acid and may additionally contain hydrogen iodide. Such a bottom fraction (or a side stream) is continuously introduced in the form of a second acetic acid stream to the next distillation column 6 via the line 34.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

To the second acetic acid stream flowing through the line 34, potassium hydroxide can be fed or added via the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a via the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a via the line 40. A portion (distillate) of the condensate portion may be recycled to the first acetic acid stream in the line 27 before introduction to the distillation column 5 from the condenser 6a via the lines 40, 41, and 42. Together with this or instead of this, a portion (distillate) of the condensate portion may be recycled to the vapor stream in the line 21 before introduction to the distillation column 3 from the condenser 6a via the lines 40, 41, and 43. Also, a portion (distillate) of the condensate portion may be recycled to the reaction vessel 1 from the condenser 6a via the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 via the recycle lines 48 and 23 and reused. In addition, a portion of the distillate from the condenser 6a may be led to various pumps (not shown) operated in the apparatus, via lines (not shown) and used as sealing solutions in these pumps. In addition, a portion of the distillate from the condenser 6a may be steadily withdrawn to the outside of the apparatus via a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a via the lines 45 and 15.

The bottom fraction withdrawn from the column bottom of the distillation column 6 via the line 39 contains a larger amount of components having a higher boiling point (higher boiling point components) than that of acetic acid as compared with the overhead stream from the distillation column 6 and contains, for example, propionic acid and potassium acetate (in the case of feeding potassium hydroxide to the line 34, etc.). Also, the bottom fraction withdrawn from the column bottom of the distillation column 6 via the line 39 also contains, for example, a corroded metal formed at and released from the inside wall of a member constituting this acetic acid production apparatus, and a compound of iodine derived from corrosive iodine and the corroded metal. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The ion exchange resin column 7 is a purification unit for performing the adsorptive removal step. This adsorptive removal step is a step for further purifying acetic acid by the adsorptive removal of, mainly, alkyl iodides (hexyl iodide, decyl iodide, etc.) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per $m^3$ resin volume ($m^3$/h)] is, for example, 3 to 15 $m^3$/h·$m^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples.

Example 1

An experiment was conducted in a bench plant based on the acetic acid production flow of FIG. 1. Methyl iodide, water, methyl acetate, acetic acid, lithium iodide, and a rhodium catalyst ([Rh(CO)$_2$I$_2$]$^-$) were fed to the reaction vessel 1 at a total pressure of 2.8 MPa (gauge pressure) and 187° C., and methanol and carbon monoxide [reaction vessel CO partial pressure (absolute pressure): 1.2 MPa] were continuously reacted to isolate a reaction mixture liquid (7.9% by mass of methyl iodide, 2.6% by mass of water, 2.0% by mass of methyl acetate, acetic acid (balance), 13.9% by mass of lithium iodide, and 910 ppm by mass of the rhodium catalyst). The obtained reaction mixture liquid was flashed [pressure: 0.15 MPa (gauge pressure), temperature: 143° C.] in the evaporator 2 shown in FIG. 2. A vapor (volatile component) from the evaporator 2 was fed to the distillation column 3 and distilled to obtain crude acetic acid as the side stream 27. The components other than the crude acetic acid were recycled to the reaction vessel 1. The composition of a residual liquid (bottom fraction) that was not volatilized in the evaporator 2 was 1.1% by mass of methyl iodide, 2.7% by mass of water, 1.1% by mass of methyl acetate, acetic acid (balance), 18% by mass of lithium iodide, and 1290 ppm by mass (based on Rh) of the rhodium catalyst. The bottom fraction of the evaporator 2 was recycled to the reaction vessel 1 via the residual liquid stream recycle lines 18 and 19 using the catalyst circulation pump 57. When the amount of the reaction mixture liquid fed to the evaporator 2 was defined as 100 parts by mass, the amount of the bottom fraction of the evaporator 2 corresponded to 76 parts by mass. The whole remaining 24 parts by mass were fed to the distillation column 3. The vent gas 15 of the reaction vessel 1 was introduced to the scrubber system 8 (in this experiment, a high-pressure absorption column). The offgas 49 (CO: 72% by mass, $H_2$: 1% by mass, $CO_2$: 8% by mass, $CH_4$: 9% by mass, $N_2$: 10% by mass) of the scrubber system 8 (high-pressure absorption column) was further fed at 0.2 NL/kg with respect to the amount of the residual liquid stream discharged (amount of the bottom fraction) of the evaporator 2 to the lower part of the vortex breaker main body 206 of the evaporator bottom part 205 via the carbon monoxide-containing gas introduction line 54.

In this operation, in the evaporator 2, the inclination angle θ of inside wall surface of the inverted truncated conical cylindrical connection portion 203 which joined the upper cylindrical portion 202 and the lower cylindrical portion 204 was set to 0° (see FIG. 2). Also, the linear velocity r of the residual liquid stream (bottom fraction) passing through the gap c between the circumferential end of the vortex breaker main body 206 and the inside bottom surface of the evaporator bottom part 205 was set to 50 m/h. The linear velocity r' of the residual liquid stream in the residual liquid stream recycle lines 18 and 19 was 2900 m/h.

In this way, 100-hour continuous operation was performed. As a result, an average Rh precipitation rate for 100 hours was 0.15 g/h. After the 100-hour experiment, the evaporator 2 and the residual liquid stream recycle line (bottom fraction line) were opened, and their insides were examined. As a result, Rh precipitation was found on the inside wall surface of the connection portion 203. However, only a very small amount of the catalyst was attached on the piping interior (inside wall surface) from the bottom of the evaporator bottom part 205 to the catalyst circulation pump 57.

The average Rh precipitation rate was determined according to the following expression:

Average Rh precipitation rate (g/h)={Total amount (g) of Rh dissolved in the system at the start of measurement−Total amount (g) of Rh dissolved in the system after 100 hours+Total amount (g) of Rh introduced from the outside of the system}/100 (h)

Example 2

The same experiment as in Example 1 was conducted except that in the evaporator 2, the θ was set to 45°, and the linear velocity r was set to 10 m/h. As a result, the average Rh precipitation rate for 100 hours was 0.15 g/h. After the 100-hour experiment, the evaporator 2 and the bottom fraction line were opened, and their insides were examined. As a result, the catalyst was not attached on the inside wall surface of the connection portion 203. However, precipitated Rh was attached on the piping interior from the bottom of the evaporator bottom part 205 to the catalyst circulation pump 57.

Example 3

The same experiment as in Example 1 was conducted except that in the evaporator 2, the θ was set to 60°, and the linear velocity r was set to 10 m/h. As a result, the average Rh precipitation rate for 100 hours was 0.08 g/h. After the 100-hour experiment, the evaporator 2 and the bottom fraction line were opened, and their insides were examined. As a result, only a very small amount of the catalyst was attached on the inside wall surface of the connection portion 203 and the piping interior from the bottom of the evaporator bottom part 205 to the catalyst circulation pump 57.

Example 4

The same experiment as in Example 1 was conducted except that in the evaporator 2, the θ was set to 60°, and the linear velocity r was set to 50 m/h. As a result, the average Rh precipitation rate for 100 hours was 0.04 g/h. After the 100-hour experiment, the evaporator 2 and the bottom fraction line were opened, and their insides were examined. As a result, Rh was not attached on the inside wall surface of the connection portion 203, and only a very small amount of the catalyst was attached on the piping interior from the bottom of the evaporator bottom part 205 to the catalyst circulation pump 57.

Example 5

The same experiment as in Example 1 was conducted except that in the evaporator 2, the θ was set to 60°, and the linear velocity r was set to 100 m/h. As a result, the average Rh precipitation rate for 100 hours was 0.02 g/h. After the 100-hour experiment, the evaporator 2 and the bottom fraction line were opened, and their insides were examined. As a result, no catalyst was attached on the inside wall surface of the connection portion 203 and the piping interior from the bottom of the evaporator bottom part 205 to the catalyst circulation pump 57.

Example 6

The same experiment as in Example 1 was conducted except that in the evaporator 2, the θ was set to 60°, and the linear velocity r was set to 300 m/h. As a result, the average Rh precipitation rate for 100 hours was 0.01 g/h. After the 100-hour experiment, the evaporator 2 and the bottom fraction line were opened, and their insides were examined. As a result, no catalyst was attached on the inside wall surface of the connection portion 203 and the piping interior from the bottom of the evaporator bottom part 205 to the catalyst circulation pump 57.

Example 7

The same experiment as in Example 1 was conducted except that in the evaporator 2, the θ was set to 60°, and the linear velocity r was set to 1000 m/h. As a result, the average Rh precipitation rate for 100 hours was 0.007 g/h. After the 100-hour experiment, the evaporator 2 and the bottom fraction line were opened, and their insides were examined. As a result, no catalyst was attached on the connection portion 203 and the piping interior from the bottom of the evaporator bottom part 205 to the catalyst circulation pump 57.

Example 8

The same experiment as in Example 1 was conducted except that in the evaporator 2, the θ was set to 60°, and the linear velocity r was set to 3000 m/h. As a result, the average Rh precipitation rate for 100 hours was 0.005 g/h. After the 100-hour experiment, the evaporator 2 and the bottom fraction line were opened, and their insides were examined. As a result, no catalyst was attached on the inside wall surface of the connection portion 203 and the piping interior from the bottom of the evaporator bottom part 205 to the catalyst circulation pump 57.

Example 9

The same experiment as in Example 1 was conducted except that in the evaporator 2, the θ was set to 60°, the linear velocity r was set to 300 m/h, and the amount of the offgas 49 fed via the carbon monoxide-containing gas introduction line 54 was set to 0.02 NL/kg with respect to the amount of the residual liquid stream discharged (amount of the bottom fraction) of the evaporator 2. As a result, the average Rh precipitation rate for 100 hours was 0.10 g/h. After the 100-hour experiment, the evaporator 2 and the bottom fraction line were opened, and their insides were examined. As a result, a very small amount of the catalyst was attached on the inside wall surface of the connection portion 203 and the piping interior from the bottom of the evaporator bottom part 205 to the catalyst circulation pump 57.

Comparative Example 1

The same experiment as in Example 1 was conducted except that in the evaporator 2, the θ was set to 0°, and the linear velocity r was set to 10 m/h. As a result, the average Rh precipitation rate for 100 hours was 0.2 g/h. After the 100-hour experiment, the evaporator 2 and the bottom fraction line were opened, and their insides were examined. As a result, fine particles of Rh were attached on the inside wall surface of the connection portion 203 and the piping interior from the bottom of the evaporator bottom part 205 to the catalyst circulation pump 57.

The configurations according to the present invention and variations or modifications thereof will be listed below as a summary of the above description.

Appendix 1: A method for producing acetic acid, comprising:

a carbonylation reaction step of reacting methanol with carbon monoxide in the presence of a catalyst system comprising a metal catalyst and methyl iodide, acetic acid, methyl acetate, and water in a reaction vessel to produce acetic acid;

an evaporation step of separating the reaction mixture obtained in the carbonylation reaction step into a vapor stream and a residual liquid stream in an evaporator;

a residual liquid stream recycle step of bringing the residual liquid stream back to the reaction vessel; and a distillation step of distilling the vapor stream to purify acetic acid, wherein the evaporator has a body part connected with a reaction mixture feed line, a top part connected with a vapor stream discharge line, and a bottom part connected with a residual liquid stream recycle line, the body part having an upper cylindrical portion having a large diameter, a lower cylindrical portion having a small diameter, and an inverted truncated conical cylindrical connection portion which joins the upper cylindrical portion and the lower cylindrical portion, and has at least one of the following catalyst precipitation and accumulation prevention structures (a) and (b):

(a) a structure where an inclination angle θ of inside wall surface of the inverted truncated conical cylindrical connection portion of the evaporator is 5° to 85°; and (b) a structure where a vortex breaker comprising a plate-like vortex breaker main body and a leg which horizontally supports the vortex breaker main body is disposed such that the vortex breaker main body covers right above the connection portion of the evaporator bottom part to the residual liquid stream recycle line, and the structure is designed such that a linear velocity r of the residual liquid stream passing through a gap between the circumferential end of the vortex breaker main body and the inside bottom surface of the evaporator bottom part is larger than 10 m/h.

Appendix 2: The method for producing acetic acid according to appendix 1, wherein the catalyst system further comprises an ionic iodide.

Appendix 3: The method for producing acetic acid according to appendix 1 or 2, wherein in the structure (a), the inclination angle θ of inside wall surface of the inverted truncated conical cylindrical connection portion of the evaporator is 10° to 80° (preferably 20° to 75°, more preferably 30° to 75°).

Appendix 4: The method for producing acetic acid according to any one of appendixes 1 to 3, wherein in the structure (b), the bottom part of the evaporator and/or the residual liquid stream recycle line is further connected with a carbon monoxide-containing gas introduction line.

Appendix 5: The method for producing acetic acid according to any one of appendixes 1 to 3, wherein in the structure (b), the bottom part of the evaporator is further connected with a carbon monoxide-containing gas introduction line.

Appendix 6: The method for producing acetic acid according to appendix 4 or 5, wherein a carbon monoxide-containing gas is introduced at not less than 0.02 NL/kg (preferably 0.02 to 5 NL/kg, more preferably 0.05 to 3 NL/kg, further preferably 0.1 to 1 NL/kg) with respect to the amount of the residual liquid stream discharged, from the carbon monoxide-containing gas introduction line.

Appendix 7: The method for producing acetic acid according to any one of appendixes 4 to 6, wherein the content of the carbon monoxide in the carbon monoxide-containing gas to be introduced is not less than 10% by mass (preferably not less than 20% by mass, more preferably not less than 40% by mass, further preferably not less than 60% by mass).

Appendix 8: The method for producing acetic acid according to any one of appendixes 1 to 7, wherein in the structure (b), a linear velocity r' of the residual liquid stream flowing through the residual liquid stream recycle line is not less than 10 m/h (preferably not less than 100 m/h, more preferably not less than 500 m/h, further preferably not less than 1000 m/h, particularly preferably not less than 2000 m/h) in not less than 80% (preferably not less than 90%, more preferably not less than 95%) of the whole channel from the bottom of the evaporator bottom part to the reaction vessel.

Appendix 9: The method for producing acetic acid according to any one of appendixes 1 to 8, wherein the distillation step comprises a lower boiling point component removal step of separating the vapor stream by distillation into an overhead stream rich in at least one lower boiling point component selected from methyl iodide and acetaldehyde and a first acetic acid stream rich in acetic acid.

Appendix 10: The method for producing acetic acid according to appendix 9, wherein the distillation step comprises a dehydration step of separating the first acetic acid stream by distillation into a second acetic acid stream more enriched with acetic acid than the first acetic acid stream, and a vapor of an overhead stream containing a larger amount of a component having a lower boiling point than that of acetic acid as compared with the second acetic acid stream.

Appendix 11: The method for producing acetic acid according to appendix 10, wherein potassium hydroxide is fed or added to the second acetic acid stream via a potassium hydroxide introduction line.

Appendix 12: The method for producing acetic acid according to appendix 10 or 11, wherein the distillation step comprises a higher boiling point component removal step of separating the second acetic acid stream by distillation into a vapor as an overhead stream containing a larger amount of a component having a lower boiling point than that of acetic acid as compared with a bottom fraction, the bottom fraction containing a larger amount of a component having a higher boiling point than that of acetic acid as compared with the overhead stream, and a third acetic acid stream more enriched with acetic acid than the second acetic acid stream.

Appendix 13: The method for producing acetic acid according to appendix 12, further comprising the step of introducing the third acetic acid stream to an ion exchange resin column so that an alkyl iodide in the third acetic acid stream is adsorptively removed.

Appendix 14: The method for producing acetic acid according to any one of appendixes 9 to 13, further comprising an acetaldehyde separation and removal step for separating at least acetaldehyde from the overhead stream obtained in the distillation step.

Appendix 15: The method for producing acetic acid according to any one of appendixes 1 to 14, further comprising a scrubber step of separating offgas from the process into a stream rich in carbon monoxide and a stream rich in acetic acid by absorption treatment with an absorption solvent containing at least acetic acid.

Appendix 16: The method for producing acetic acid according to appendix 15, wherein in the structure (b), the bottom part of the evaporator and/or the residual liquid stream recycle line is connected with a carbon monoxide-containing gas introduction line, and the stream rich in carbon monoxide separated in the scrubber step is used as a CO source that is introduced to the bottom part of the evaporator and/or the residual liquid stream recycle line.

Appendix 17: The method for producing acetic acid according to any one of appendixes 1 to 16, wherein in the structure (b), the linear velocity r is adjusted by changing the length of the gap between the circumferential end of the vortex breaker main body and the inside bottom surface of the evaporator bottom part, and/or the circumferential length of the vortex breaker main body.

Appendix 18: The method for producing acetic acid according to any one of appendixes 1 to 17, wherein the internal pressure of the evaporator is 50 to 1000 kPa (absolute pressure).

Appendix 19: The method for producing acetic acid according to any one of appendixes 1 to 18, wherein the ratio between the vapor stream and the residual liquid stream to be separated in the evaporation step is 10/90 to 50/50 (vapor stream/residual liquid stream) in terms of a mass ratio.

Appendix 20: The method for producing acetic acid according to any one of appendixes 1 to 19, wherein the acetic acid concentration of the vapor stream separated in the evaporation step is 50 to 85% by mass (preferably 55 to 75% by mass).

Appendix 21: The method for producing acetic acid according to any one of appendixes 1 to 20, wherein the acetic acid concentration of the residual liquid stream separated in the evaporation step is 55 to 90% by mass (preferably 60 to 85% by mass).

Appendix 22: The method for producing acetic acid according to any one of appendixes 1 to 21, wherein the evaporator has the structure (b).

Appendix 23: The method for producing acetic acid according to any one of appendixes 1 to 22, wherein the evaporator has both of the structure (a) and the structure (b).

INDUSTRIAL APPLICABILITY

The method for producing acetic acid of the present invention can be used as industrial method for producing acetic acid by carbonylation process of a methanol method (acetic acid process of a methanol method).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
201: evaporator top part
202: upper cylindrical portion of an evaporator body part
203: connection portion of the evaporator body part
204: lower cylindrical portion of the evaporator body part
205: evaporator bottom part
206: vortex breaker main body
207: leg
c: gap
x: vortex breaker

The invention claimed is:
1. A method for producing acetic acid, comprising:
a carbonylation reaction step of reacting methanol with carbon monoxide in the presence of a catalyst system comprising a metal catalyst and methyl iodide, acetic acid, methyl acetate, and water in a reaction vessel to produce acetic acid;
an evaporation step of separating the reaction mixture obtained in the carbonylation reaction step into a vapor stream and a residual liquid stream in an evaporator;
a residual liquid stream recycle step of bringing the residual liquid stream back to the reaction vessel; and
a distillation step of distilling the vapor stream to purify acetic acid, wherein
the evaporator has a body part connected with a reaction mixture feed line, a top part connected with a vapor stream discharge line, and a bottom part connected with a residual liquid stream recycle line, the body part having an upper cylindrical portion having a large diameter, a lower cylindrical portion having a small diameter, and an inverted truncated conical cylindrical connection portion which joins the upper cylindrical portion and the lower cylindrical portion, and has the following catalyst precipitation and accumulation prevention structures of both (a) and (b):

(a) a structure where an inclination angle θ of inside wall surface of the inverted truncated conical cylindrical connection portion of the evaporator is 5° to 85°; and (b) a structure where a vortex breaker comprising a plate-like vortex breaker main body and a leg which horizontally supports the vortex breaker main body is disposed such that the vortex breaker main body covers right above the connection portion of the evaporator bottom part to the residual liquid stream recycle line, and the structure is designed such that a linear velocity r of the residual liquid stream passing through a gap between the circumferential end of the vortex breaker main body and the inside bottom surface of the evaporator bottom part is larger than 10 m/h.

2. The method for producing acetic acid according to claim 1, wherein the catalyst system further comprises an ionic iodide.

3. The method for producing acetic acid according to claim 1, wherein in the structure (a), the inclination angle θ of inside wall surface of the inverted truncated conical cylindrical connection portion of the evaporator is 10° to 80°.

4. The method for producing acetic acid according to claim 1, wherein in the structure (b), the bottom part of the evaporator and/or the residual liquid stream recycle line is further connected with a carbon monoxide-containing gas introduction line.

5. The method for producing acetic acid according to claim 4, wherein a carbon monoxide-containing gas is introduced at not less than 0.02 NL/kg with respect to the amount of the residual liquid stream discharged, from the carbon monoxide-containing gas introduction line.

6. The method for producing acetic acid according to claim 1, wherein in the structure (b), a linear velocity r' of the residual liquid stream flowing through the residual liquid stream recycle line is not less than 10 m/h in not less than 80% of the whole channel from the bottom of the evaporator bottom part to the reaction vessel.

7. The method for producing acetic acid according to claim 1, wherein the distillation step comprises a lower boiling point component removal step of separating the vapor stream by distillation into an overhead stream rich in at least one lower boiling point component selected from methyl iodide and acetaldehyde and an acetic acid stream rich in acetic acid.

8. The method for producing acetic acid according to claim 7, further comprising an acetaldehyde separation and removal step for separating at least acetaldehyde from the overhead stream.

9. The method for producing acetic acid according to claim 1, further comprising a scrubber step of separating offgas from the process into a stream rich in carbon monoxide and a stream rich in acetic acid by absorption treatment with an absorption solvent containing at least acetic acid.

* * * * *